US006291431B1

(12) United States Patent
Balaban et al.

(10) Patent No.: US 6,291,431 B1
(45) Date of Patent: Sep. 18, 2001

(54) METHODS AND COMPOSITIONS FOR THE TREATMENT AND PREVENTION OF STAPHYLOCOCCAL INFECTIONS

(75) Inventors: Naomi Balaban, Davis; James W. Larrick, Woodside; Susan C. Wright, Saratoga, all of CA (US)

(73) Assignees: Panorama Research, Mountain View; The Regents of the University of California, Oakland, both of CA (US)

( * ) Notice: Subject to any disclaimer, the term of this patent is extended or adjusted under 35 U.S.C. 154(b) by 96 days.

(21) Appl. No.: 09/054,331

(22) Filed: Apr. 2, 1998

Related U.S. Application Data (60) Provisional application No. 60/068,094, filed on Dec. 19, 1997.

(51) Int. Cl.[7] .......................... A61K 38/00; A61K 38/02; C07K 5/00; C07K 7/00
(52) U.S. Cl. .............................. 514/16; 514/12; 530/300; 530/329; 424/185.1; 424/520
(58) Field of Search .................... 514/12, 16; 424/185.1, 424/520; 530/300, 329

(56) References Cited

FOREIGN PATENT DOCUMENTS

| WO96/10579 | 4/1996 | (WO) . |
| WO97/44349 | 11/1997 | (WO) . |

OTHER PUBLICATIONS

Ji, et al. "Cell Density Control of *Staphylococcus* Virulence Mediated by an Octapeptide Pheromone," *Proc. Natl. Acad. Sci. USA* (1995) 92:12055–12059.

Ji, et al. "Bacterial Interference Caused by Autoinducing Peptide Variants" *Science* (1997) 276:2027–2030.

Mayville, et al. "Structure–Activity Analysis of Synthetic Autoinducing Thiolactone Peptides form *Staphylococcus Aureus* Responsible for Virulence," *Proc. Natl. Acad. Sci. USA* (1999) 96:1218–1223.

Novick, et al., "Virulence Gene Regulation by Peptides in *Staphylococci* and other Gram–positive Bacteria," *Curr. Opin. in Microbiol.* (1999) 2:40–45.

Balaban et al, *PNAS*, (1995), vol. 92 No. 5, pp. 1619–1623.*

Balaban et al., *Science*, 1998, vol. 280, No. 5362 pp. 438–440.*

Balaban et al. "Autocrine regulation of toxin synthesis by *Staphylococcus aureas*" Proc. Natl. Acad. Sci. USA (1995) 92:1619–1623.

Balaban et al., "Translation of RNAIII, the *Stahylococcus aureas* agr regulatory RNA molecule, can be activated by a 3'–end deletion" FEMS Microbiol. Letters (1995) 133:155–161.

Morfeldt et al., "Activation of alpha–toxin translation in *Staphylococcus aureus* by the trans–encoded antisense RNA, RNAIII" EMBO Journal (1995) 14(18):4569–4577.

Novick et al., "Synthesis of staphylococcal virulence factors is controlled by a regulatory RNA molecule" EMBO Journal (1993) 12(120):3967–3975.

Panlilio et al., "Methicillin–resistant *Staphylococcus aureus* in U.S. hospitals, 1875–1991" Infect. Control Hosp. Epidemiol. (1992) 13:582–586.

Silverstein et al., "Host Defense against bacterial and fungal infections" Microbiology, Fourth Edition, J.B. Lippincott Company, Philadelphia, B.D. Davis et al., Eds., Chapter 21, pp. 485–505.

* cited by examiner

*Primary Examiner*—Avis M. Davenport
(74) *Attorney, Agent, or Firm*—Bozicevic, Field & Francis LLP; Carol L. Francis

(57) ABSTRACT

Methods and compositions are provided for the treatment of staphylococcal infections.

26 Claims, 5 Drawing Sheets

SEQUENCE LISTING

<160> NUMBER OF SEQ ID NOS: 11

<210> SEQ ID NO 1
<211> LENGTH: 7
<212> TYPE: PRT
<213> ORGANISM: S. aureus
<220> FEATURE:
<221> NAME/KEY: VARIANT
<222> LOCATION: (1)...(7)
<223> OTHER INFORMATION: Xaa = Cys, Trp or Ile

<400> SEQUENCE: 1

Tyr Lys Pro Xaa Thr Asn Phe
 1               5

<210> SEQ ID NO 2
<211> LENGTH: 7
<212> TYPE: PRT
<213> ORGANISM: S. aureus
<220> FEATURE:
<221> NAME/KEY: VARIANT
<222> LOCATION: (1)...(7)
<223> OTHER INFORMATION: Xaa = Cys, Trp or Ile

<400> SEQUENCE: 2

Tyr Ser Pro Xaa Thr Asn Phe
 1               5

<210> SEQ ID NO 3
<211> LENGTH: 10
<212> TYPE: PRT
<213> ORGANISM: S. aureus
<220> FEATURE:
<221> NAME/KEY: VARIANT
<222> LOCATION: (1)...(10)
<223> OTHER INFORMATION: Xaa = Cys, Trp or Ile

<400> SEQUENCE: 3

Ile Lys Lys Tyr Lys Pro Xaa Thr Asn Phe
 1               5                  10

<210> SEQ ID NO 4
<211> LENGTH: 10
<212> TYPE: PRT
<213> ORGANISM: S. aureus
<220> FEATURE:
<221> NAME/KEY: VARIANT
<222> LOCATION: (1)...(10)
<223> OTHER INFORMATION: Xaa = Cys, Trp or Ile

<400> SEQUENCE: 4

Ile Lys Lys Tyr Ser Pro Xaa Thr Asn Phe
 1               5                  10

<210> SEQ ID NO 5
<211> LENGTH: 21
<212> TYPE: DNA
<213> ORGANISM: S. aureus

<400> SEQUENCE: 5
tattcgccgt ggaccaattt t                                             21

<210> SEQ ID NO 6
<211> LENGTH: 9
<212> TYPE: PRT
<213> ORGANISM: S. aureus

```
<400> SEQUENCE: 6

Ile Lys Lys Tyr Lys Pro Ile Thr Asn
1               5

<210> SEQ ID NO 7
<211> LENGTH: 7
<212> TYPE: PRT
<213> ORGANISM: Artificial Sequence
<220> FEATURE:
<223> OTHER INFORMATION: synthetic peptide

<400> SEQUENCE: 7

Tyr Ser Pro Trp Thr Asn Phe
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic peptide

<400> SEQUENCE: 8

Pro Cys Thr Asn Phe
1               5

<210> SEQ ID NO 9
<211> LENGTH: 7
<212> TYPE: PRT
<213> ORGANISM: S. aureus

<400> SEQUENCE: 9

Tyr Lys Pro Ile Thr Asn Phe
1               5

<210> SEQ ID NO 10
<211> LENGTH: 7
<212> TYPE: PRT
<213> ORGANISM: Artificial Sequence
<220> FEATURE:
<223> OTHER INFORMATION: synthetic peptide

<400> SEQUENCE: 10

Tyr Ser Pro Ile Thr Asn Phe
1               5

<210> SEQ ID NO 11
<211> LENGTH: 7
<212> TYPE: PRT
<213> ORGANISM: Artificial Sequence
<220> FEATURE:
<223> OTHER INFORMATION: synthetic peptide

<400> SEQUENCE: 11

Tyr Lys Pro Trp Thr Asn Phe
1               5
```

METHODS AND COMPOSITIONS FOR THE TREATMENT AND PREVENTION OF STAPHYLOCOCCAL INFECTIONS

This application is a continuation-in-part of U.S. Ser. No. 60/068,094, filed Dec. 19, 1997, the specification of which is incorporated by reference in its entirety herein for all purpose.

BACKGROUND OF THE INVENTION

*Staphylococcus aureus* causes diseases chiefly through the production of virulence factors such as hemolysins, enterotoxins and toxic shock syndrome toxin. The synthesis of virulence factors in *S. aureus* is controlled by a regulatory RNA molecule, RNAIII (Novick, et al., *EMBO J.* 12, 3967 (1993), Balaban et al., *FEMS Microbiol. Letts.* 133, 155 (1995), Moerfeldt et al., *EMBO J.* 14, 4569 (1995)), encoded by the agr locus. The rnaiii gene of the agr locus is transcribed in culture only from the midexponential phase of growth, and is autoinduced by the protein RNAIII activating protein (RAP)(Balaban et al., *Proc. Natl. Acad. Sci. U.S.A.* 92, 1619 (1995)). RAP is continuously secreted by the bacteria and only activates RNAIII at a concentration threshold (ibid).

Antibodies to RAP block the activation of rnaiii in vitro. A peptide, termed RNAIII inhibiting peptide (RIP) is produced by a nonpathogenic strain of *S. aureus* mutated by nitrosoguanidine (ibid). RIP competes with RAP for the activation of RNAIII, and thus inhibits toxin production by *S. aureus* (ibid).

*Staphylococcus aureus* causes diseases ranging from minor skin infections to life-threatening deep infections such as pneumonia, endocarditis, meningitis, post-operative wound infections, septicemia, and toxic shock syndrome (Silverstein et al., in *Microbiology*, Davis et al., eds. (Lippincott, Philadelphia, 1990), pp. 485–506). Hospitalized patients are at particular risk, with over 500,000 nosocomial infections per year (Panlilio, et al., *Inf. Contr. and Hosp. Epidem.* 13, 582 (1992)). The emergence of drug resistance has made many of the available antimicrobial agents ineffective. Therefore, alternative methods for the prevention and treatment of bacterial infections in general and *S. aureus* infections in particular are eagerly sought. The instant invention addresses this need and others.

SUMMARY OF THE INVENTION

One aspect of the invention is a composition comprising a polypeptide comprising an amino acid sequence comprising the general formula Y(K or S) PXTNF (SEQ ID NOS:1 and 2), where X is C, W, or I. Pharmaceutical compositions are also provided in some embodiments.

A further aspect of the invention is a composition of claim 1, wherein the polypeptide comprises an amino acid sequence comprising the general formula IKKY(K or S) PXTNF (SEQ ID NOS:3 and 4), where X is C, W, or I.

A further aspect of the invention is a method for treating a host for a staphylococcal infection, wherein the composition of claim 1 is administered to the host. In some embodiments the host is a human patient. In further embodiments the host is an animal, such as but not limited to an experimental animal.

A further aspect of the invention is a method for treating a host for a staphylococcal infection, wherein an antagonist of the RAP receptor is administered to the host. In some embodiments the host is a human patient. In further embodiments the host is an animal, such as but not limited to an experimental animal. In some embodiments the antagonist is a polypeptide, a peptidomimetic, or an antibody.

A further aspect of the invention is a nucleic acid molecule encoding a polypeptide of the invention. The nucleic acid molecule can be RNA or DNA or an antisense nucleic acid molecule. In an embodiment, the nucleic acid molecule comprises the nucleotide sequence TAT TCG CCG TGG ACC AAT TTT (SEQ ID NO:5).

BRIEF DESCRIPTION OF THE FIGURES

FIG. 1 comprises Panels A–D.

FIG. 1A is a graph depicting an assay for RNAIII activation as described in Balaban et al. (supra). Postexponential supernatants of wild-type *S. aureus* (denoted total) were filtered through a 3-kD cutoff membrane and the flow-through containing agrD-encoded octapeptide (Guangyong, el al., *Proc. Natl. Acad. Sci. U.S.A.* 92, 12055 (1995)) collected (denoted <3-kD). Retained material (containing RAP) was filtered through a 10-kD cutoff membrane. Material greater than 10-kD (denoted >10-kD) was applied to an HPLC gel filtration column and purified RAP was collected (RAP). Increasing amounts of each of these compositions were added to early exponential wild type *S. aureus* and tested for their ability to activate RNAIII.

FIG. 2A is a photograph of an immunoblot of sera of vaccinated and control animals. Postexponential supernatant of wild type *S. aureus* (Lanes 1,2) or purified RAP (Lane 3) was separated on SDS 12% PAGE, western blotted, and membranes were incubated in the presence of: Lane 1: pre-immune (lane 1a) or post-immune (lane 1b) sera collected from a control CFA-injected animal (diluted 1:20). Lane 2: pre-immune sera (lane 2a, diluted 1:20) or post immune sera (lane 2b diluted 1:1000 and lane 3 diluted 1:20). Approximate molecular weight markers are indicated in kilodaltons.

FIG. 4 comprises panels 4A–C.

DETAILED DESCRIPTION OF THE INVENTION

Generally, the nomenclature used hereafter, and the laboratory procedures in cell culture and protein biochemistry are those well known and commonly employed in the art. Generally, enzymatic reactions and column chromatography are performed according the manufacturer's specifications.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For the purposes of the present invention, the foregoing terms are defined below.

The terms "pharmaceutically acceptable" or "therapeutically acceptable" refer to a substance which does not interfere with the effectiveness or the biological activity of the active ingredients and which is not toxic to the host or the patient.

The terms "encoding" or "encodes" refer generally to the sequence information being present in a translatable form, usually operably linked to a promoter. A sequence is operably linked to a promoter when the functional promoter enhances transcription or expression of that sequence. An anti-sense strand is considered to also encode the sequence, since the same informational content is present in a readily accessible form, especially when linked to a sequence which promotes expression of the sense strand. The information is convertible using the standard, or a modified, genetic code. See, e.g. Watson et al., (1987) *The Molecular Biology of the Gene,* (4th Edition), Vols. 1 & 2, Benjamin, Menlo Park, Calif.

As used to refer to nucleic acid sequences, the term "homologous" indicates that two or more nucleotide sequences share a majority of their sequence. Generally, this will be at least about 70% of their sequence and preferably at least 95% of their sequence. Another indication that sequences are substantially identical is if they hybridize to the same nucleotide sequence under stringent conditions (see, e.g., Sambrook et al., *Molecular Cloning—A Laboratory Manual,* Cold Spring Harbor Laboratory, Cold Spring Harbor, N.Y., 1985). Stringent conditions are sequence-dependent and will be different in different circumstances. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C.

As used to refer to proteins, polypeptides, or peptides, which terms are used interchangeably here, the term "homologous" is meant to indicate two proteins or polypeptides share a majority of their amino acid sequences. Generally, this will be at least 90% and usually more than about 95%. Homology for polypeptides or proteins is typically measured using sequence analysis software, see e.g. Sequence Analysis Software Package of the Genetics Computer Group, University of Wisconsin Biotechnology Center, 1710 University Avenue, Madison, Wis. 53705. Protein analysis software matches similar sequences using measure of homology assigned to various substitutions, deletions, and other modifications. Conservative substitutions typically include substitutions within the following groups glycine, alanine; valine, isoleucine, leucine; aspartic acid, glutamic acid; asparagine, glutamine; serine, threonine; lysine, arginine; and phenylalanine, tyrosine.

The term "isolated" as applied to nucleic acids, means a nucleic acid substantially separated from other macromolecules, cellular components, or DNA sequences which naturally accompany a native nucleic acid, e.g. ribosomes, polymerases, other nucleic acid sequences, and the like. The term includes a nucleic acid that has been removed from its naturally occurring environment, and includes recombinant or cloned DNA isolates and chemically synthesized analogues, and analogues biologically synthesized by heterologous systems. A substantially pure or biologically pure nucleic acid includes isolated forms of the nucleic acid.

The phrase "biologically pure" or "substantially pure" refers to material that is substantially or essentially free from components which normally accompany it as found in its native state.

The term "recombinant" refers to a nucleic acid sequence which is not naturally occurring, or is made by the artificial combination of two otherwise separated segments of sequence, i.e. by chemical synthesis, genetic engineering, and the like.

The instant invention provides polypeptides for the prevention and treatment of *S. aureus* infections. These polypeptides comprise the general formula Y(K or S) PXTNF (SEQ ID NOS:5), where X is C, W, or I, preferably W. In a further embodiment, the polypeptides may have the general formula IKKY(K or S) PXTNF (SEQ ID NOS:3 and 4), where X is C, W, or I, preferably W. The polypeptides are preferably at least 10 amino acids in length, more preferably at least seven amino acids in length.

Nucleic acids encoding the polypeptides of the invention are also included in the scope of the invention. Such nucleic acids may be DNA, RNA, or antisense nucleic acids. In an embodiment an isolated DNA molecule of the invention comprises the sequence TAT TCG CCG TGG ACC AAT TTT (SEQ ID NO:5). The nucleic acid molecules of the invention may be provided as synthetic or purified, isolated molecules, including but not limited to "naked DNA"; in vectors such as but not limited to plasmids or viruses, including expression vectors, or complexed to other compounds for administration. Such techniques are well known in the art.

The polypeptides of the invention are preferably synthesized de novo by any technique commonly known in the art or may be encoded by nucleic acid, such as RNA or DNA, delivered to the host. Purification from cultures of *S. aureus* bacteria is discussed in the Experimental section below.

The polypeptides of the invention are typically administered to hosts having or at risk of having a staphylococcal infection such as an *S. aureus* infection. The hosts are typically human patients. Animals may also be treated with the compositions of the invention, including but not limited to animals of commercial or veterinary importance such as cows, sheep, and pigs, and experimental animals such as rats, mice, or guinea pigs.

Typically, the compositions of the invention are administered on a daily basis for at least a period of 1–5 days. As used herein, "therapeutic dose" is a dose which prevents, alleviates, abates, or otherwise reduces the severity of symptoms in a patient. The compositions of the invention may be used prophylactically to prevent staphylococcal infections or may be therapeutically used after the onset of symptoms. In some embodiments, induction of the formation of antibodies to the administered compound is desirable. In such instances, standard immunization protocols used in the art are preferred. The compositions administered for immunization may optionally include adjuvants.

In some embodiments of the invention, antagonists of the RAP receptor are provided. Without being limited to any one theory, RIP may function by competing with RAP for binding to the RAP receptor, thus acting as an antagonist of the RAP receptor. Such antagonists include but are not limited to antibodies which specifically bind to RAP; antibodies which specifically bind to a RAP ligand; ligands for RAP or RIP; antisense nucleic acids; and peptide, non-peptide, and peptidomimetic analogs of RAP, RIP, and their ligands.

Antibodies can be synthetic, monoclonal, or polyclonal and can be made by techniques well known in the art. For therapeutic applications, "human" monoclonal antibodies having human constant and variable regions are often preferred so as to minimize the immune response of a patient against the antibody. Such antibodies can be generated by immunizing transgenic animals which contain human immunoglobulin genes. See Jakobovits et al. *Ann NY Acad Sci* 764:525–535 (1995). In connection with synthetic and semi-synthetic antibodies, such terms are intended to cover but are not limited to antibody fragments, isotype switched antibodies, humanized antibodies (e.g., mouse-human, human-mouse, and the like), hybrids, antibodies having plural specificities, filly synthetic antibody-like molecules, and the like.

As discussed below, antibodies can be screened for the ability to block the binding of a ligand to RAP or RIP and/or for other properties, such as the ability to protect in vivo against *S. aureus* infection.

In some embodiments of the invention, antisense nucleic acid molecules are used as antagonists of RAP. Antisense nucleic acid molecules are complementary oligonucleotide strands of nucleic acids designed to bind to a specific sequence of nucleotides to inhibit production of a targeted protein. These agents may be used alone or in combination with other antagonists. The antisense antagonist may be provided as an antisense oligonucleotide such as RNA (see, for example, Murayama et al. *Antisense Nucleic Acid Drug Dev.* 7:109–114(1997)). Antisense genes may also be provided in a viral vector, such as, for example, in hepatitis B virus (see, for example, Ji et al., *J. Viral Hepat.* 4:167–173 (997)); in adeno-associated virus (see, for example, Xiao et al. *Brain Res.* 756:76–83 (1997)); or in other systems including but not limited to an HVJ(Sendai virus)-liposome gene delivery system (see, for example, Kaneda et at. *Ann. N.Y. Acad. Sci.* 811:299–308 (1997)); a "peptide vector" (see, for example, Vidal et al. *CR Acad. Sci III* 32): 279–287 (1997)); as a gene in an episomal or plasmid vector (see, for example, Cooper et al. *Proc. Natl. Acad. Sci. U.S.A.* 94:6450–6455 (1997), Yew et al. *Hum Gene Ther.* 8:575–584 (1997)); as a gene in a peptide-DNA aggregate (see, for example, Nildome et al. *J. Biol. Chem.* 272:15307–15312 (1997)); as "naked DNA" (see, for example, U.S. Pat. Nos. 5,580,859 and 5,589,466); and in lipidic vector systems (see, for example, Lee et al. *Crit Rev Ther Drug Carrier Syst.* 14:173–206 (1997)).

Candidate antagonists of the RAP receptor can be screened for function by a variety of techniques known in the art and/or disclosed within the instant application, such as protection against *S. aureus* infection in a mouse model.

A multitude of appropriate formulations of the antagonists of the invention can be found in the formulary known to all pharmaceutical chemists: Remington's *Pharmaceutical Sciences,* (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human dosage. Various considerations are described, for example, in Goodman and Gilman's *The Pharmacological Basis of Therapeutics,* 7th Edition (1985), MacMillan Publishing Company, New York, and Remington's *Pharmaceutical Sciences* 18th Edition, (1990) Mack Publishing Co, Easton, Pa. Methods for administration are discussed therein, including oral, intravenous, intraperitoneal, intramuscular, transdermal, nasal, ionto-phoretic administration, and the like.

The compositions of the invention may be administered in a variety of unit dosage forms depending on the method of administration. For example, unit dosage forms suitable for oral administration include solid dosage forms such as powder, tablets, pills, capsules, and dragees, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may also be administered via liposomes. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule which binds to a desired target, such as antibody, or with other therapeutic or immunogenic compositions. Thus, liposomes either filled or decorated with a desired composition of the invention of the invention can delivered systemically, or can be directed to a tissue of interest, where the liposomes then deliver the selected therapeutic/immunogenic polypeptide compositions.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. *Ann. Rev. Biophys. Bioeng.* 9:467 (1980), U.S. Pat. Nos. 4,235,871, 4,501,728, 4,837,028, and 5,019,369, incorporated herein by reference.

A liposome suspension containing a composition of the invention may be administered intravenously, locally, topically, etc. in a dose which varies according to, inter alia, the manner of administration, the composition of the invention being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more compositions of the invention of the invention, and more preferably at a concentration of 25%–75%.

For aerosol administration, the compositions of the invention are preferably supplied in finely divided form along with a surfactant and propellant. Typical percentages of compositions of the invention are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

The constructs of the invention can additionally be delivered in a depot-type system, an encapsulated form, or an implant by techniques well-known in the art. Similarly, the constructs can be delivered via a pump to a tissue of interest.

Any of the foregoing formulations may be appropriate in treatments and therapies in accordance with the present invention, provided that the active agent in the formulation is not inactivated by the formulation and the formulation is physiologically compatible.

Polyclonal and/or monoclonal antibodies to the polypeptides of the present invention may be prepared. The polypeptides of the invention thereof may be prepared as described herein, and coupled to a carrier molecule, for example keyhole limpet hemocyanin, and injected into rabbits at selected times over several months. The rabbit sera may be tested for immunoreactivity to the polypeptides thereof Monoclonal antibodies may be made by injecting mice with the polypeptides. Monoclonal antibodies may be screened by methods known in the art, as are described, for example, in Harlow and Lane (1988) *Antibodies: A laboratory manual,* Cold Spring Harbor Press, New York, and Goding (1986) *Monoclonal antibodies: Principles and Practice* (2d ed.) Academic Press, New York. The antibodies will be tested for specific immunoreactivity with an epitope of the polypeptides. These antibodies will find use in diagnostic assays or as an active ingredient in a pharmaceutical composition.

For production of polyclonal antibodies, an appropriate target immune system is selected, typically a mouse or rabbit, although other species such as goats, sheep, cows, guinea pigs, and rats may be used. The substantially purified antigen is presented to the immune system according to methods known in the art. The immunological response is typically assayed by an immunoassay. Suitable examples include ELISA, RIA, fluorescent assay, or the like. These antibodies will find use in diagnostic assays or as an active ingredient in a pharmaceutical composition.

The following examples are intended to illustrate, not limit the scope of this invention.

EXPERIMENTAL EXAMPLES

I. In vivo studies in mice

A. Purification of RAP

Figure 1A:
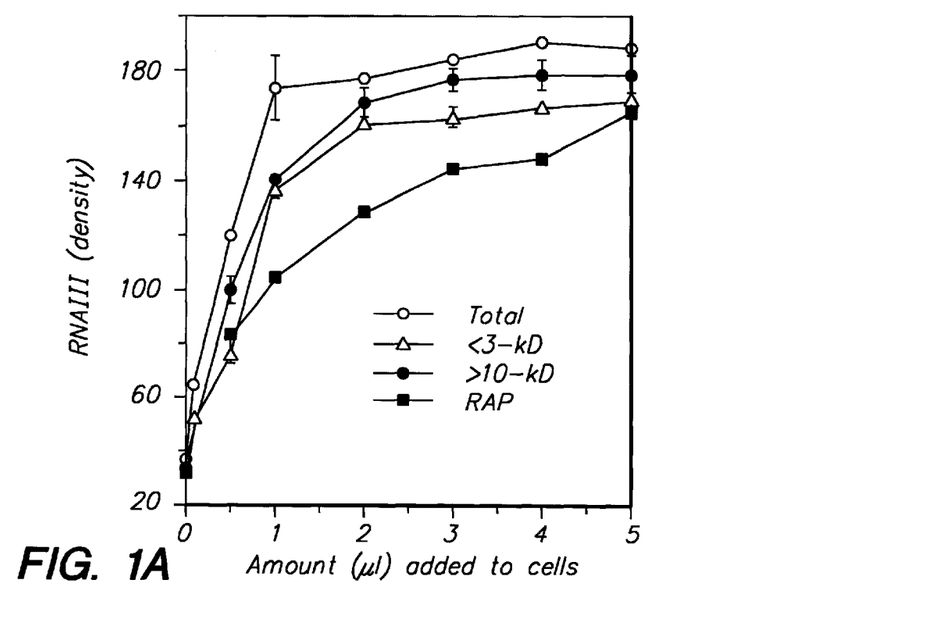
Figure 1B:
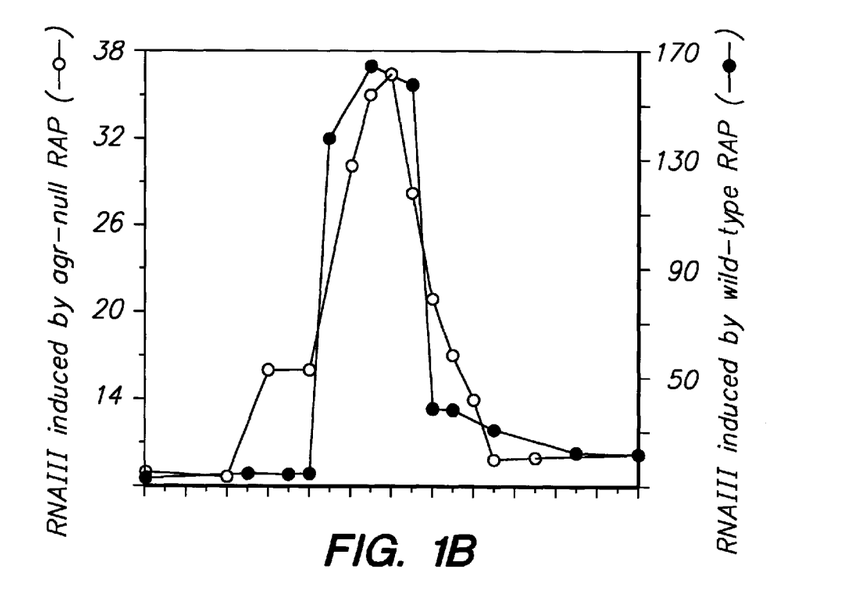
FIG. 1B is a graph depicting the ability of 1 ml fractions collected from postexponential supernatants of wild type *S. aureus* and of agr-null *S. aureus* fractionated on a gel filtration to activate RNAIII.
Figure 1C:
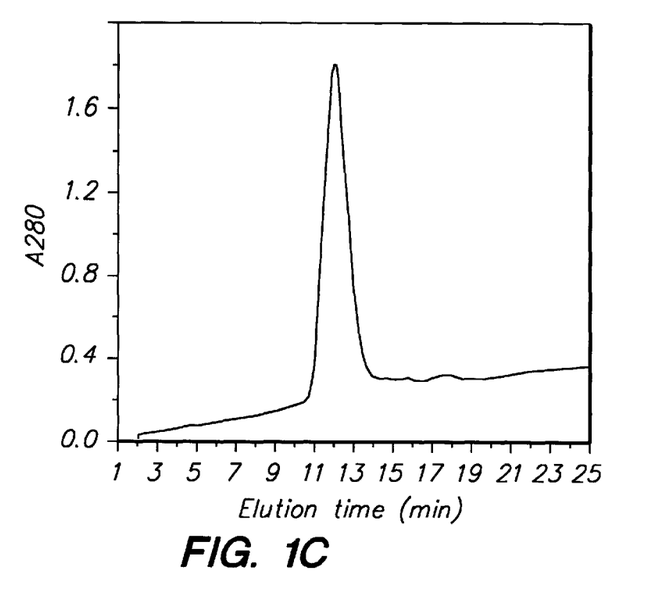
FIG. 1C is a graph depicting the absorbance at A280 of fractions from FIG. 1B containing peak RNAIII-inducing activity.
Figure 1D:
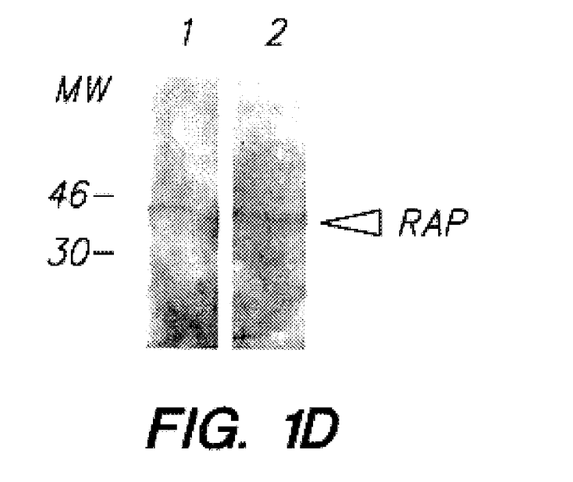
FIG. 1D is a photograph of gel-filtration-purified RAP from wild type (lane 1) and from agr-null strain (lane 2) separated on SDS PAGE and silver stained. Approximate molecular weight markers are indicated.

In these experiments RAP was purified from post exponential supernatants of wild-type *S. aureus* (FIG. 1) as described by Balaban et al. (*Proc. Natl. Acad. Sci. U.S.A.* 92, 1619 (1995)). Peak fractions (FIGS. 1B,C) contained a protein of about 38 kD (FIG. 1D). HPLC-purified RAP was run on SDS PAGE, blotted onto a PVDF membrane, Coomassie stained, and the purified 38-kD protein used for N-terminal sequencing by Edman degradation. The $NH_2$-terminal sequence of RAP was determined to be IKKYK-PITN (SEQ ID NO:6). This sequence showed no significant homology to known proteins.

We also purified RAP from post exponential supernatants of an agr-null strain in which the entire agr locus was replaced with the tetM marker (Novick et al. *EMBO J.* 12:3967 (1993)), which suggests that RAP is independent of agr.

B. Immunization with RAP

To test whether immunization with RAP can inhibit *S. aureus* infection, we used the murine model of cutaneous infection (Bunce et al., *Infect. Immun.*60, 2636 (1992)). In this model, when the wild-type Smith diffuse (SD) strain of *S. aureus* is injected subcutaneously together with dextran beads (Cytodex), a visible, measurable lesion (cellulitis) is induced after 24 hrs. In contrast, no lesion is induced in animals injected with cytodex beads alone.

Four-eight week old (20–30 g), outbred, immunocompetent, hairless male mice, strain Crl:SKH1 (hrhr)Br were obtained from Charles River, Wilmington, Mass. and used for these experiments. For prophylactic vaccination with RAP (purified from a wild type *S. aureus* strain) or RAP* (purified from an agr-null), 10 μg RAP, purified on a gel filtration column as described by Balaban et al. (supra), was injected together with complete Freund's adjuvant (CFA) on first injection and incomplete Freund's adjuvant (ICFA) on second and third injection subcutaneously, into 4 week old male hairless immunocompetent mice on days 0, 7 and 21. Control mice were either injected with the adjuvant alone or not injected at all (untreated). Vaccinated and control mice were challenged on day 31 with $1.24 \times 10^8$ Smith Diffuse *S. aureus* subcutaneously together with 1 mg cytodex beads (10) to induce a local infection. The size of the lesion was measured daily and presented as area=0.5 {p(length) (width)}(Table 1). FIG. 5 depicts the typical appearances of control or protected mice (top mouse) and mice which developed cellulitis (bottom mouse).

After challenge with *S. aureus,* 72% (24/33) RAP-vaccinated mice remained free of disease as compared to 30% (3/10) controls immunized with complete Freund's adjuvant (CEA) and 0% of untreated controls. This difference was statistically significant (RAP vs untreated:

p<0.0001; RAP vs CFA: p=0.0031) using Fisher's exact probability test. Fisher's Exact Probability Test was used to compare proportions of mice developing lesions and mice developing anti-RAP antibodies among the experimental groups (RAP-vaccinated, CFA controls, untreated controls). Among animals developing lesions post challenge with *S. aureus,* the size of the lesions was compared using singe factor Analysis of Variance. Post-hoc testing was performed using Fisher's protected least significant difference.

In addition, in mice that developed lesions, the mean lesion size was 50% smaller than that of CFA control mice (177 mm$^2$) and 76% smaller than untreated controls (370 mm$^2$). Animals that died had extensive lesions which spread to over one quarter of their body size. Only 3% (1/33) of RAP-vaccinated animals died as a result of challenge whereas 22% of control animals died (5/22).

Figure 2A:
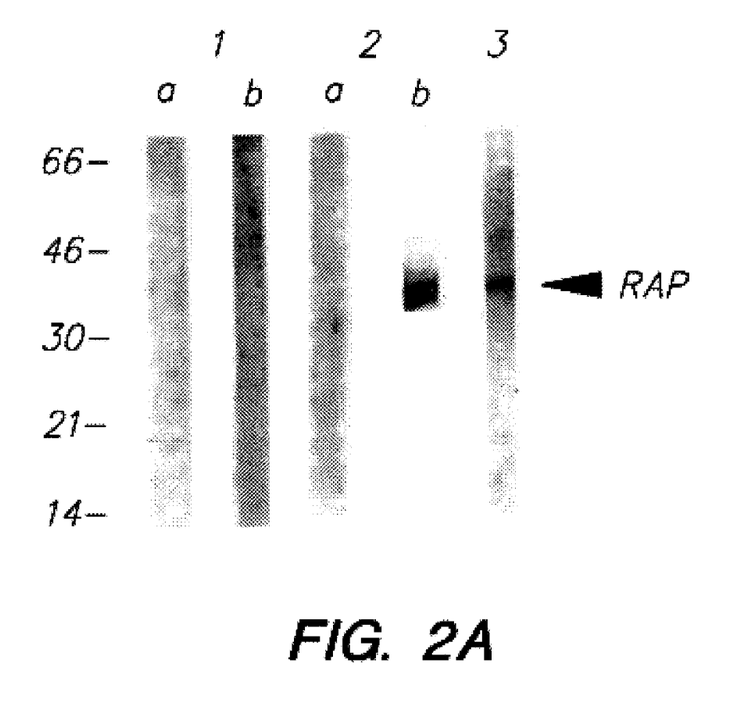

To determine if antibodies to RAP were generated, sera from vaccinated and control animals were analyzed by immunoblotting (FIG. 2A) and binding activity to wild-type *S. aureus* post-exponential supernatants that contained RAP. To estimate antibody levels against the injected antigen, a drop of blood (50 μl) was collected from the tip of the tail before vaccination (pre-immune sera) and 7 days after the third vaccination period (post immune sera, 3 days before bacterial challenge). Anti-RAP antibody titer was determined by western blotting. Sera was added to the blot (containing postexponential supernatants) in increasing dilutions, until no band appeared. The highest dilution which still reacted with RAP was the determined titer. Animals vaccinated with RAP developed antibodies to a 38-kD protein, and could also bind to purified RAP.

Figure 2B:
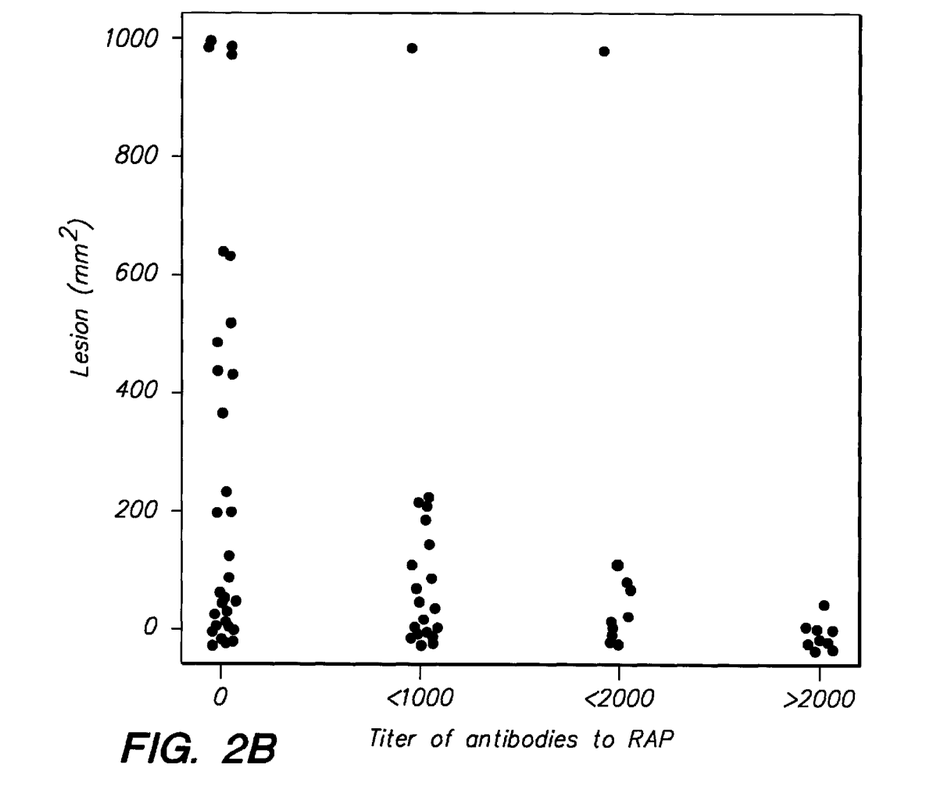
FIG. 2B is a graph depicting the titer of anti-RAP antibodies vs lesion size of vaccinated animals.

Most (33/34) vaccinated animals developed antibodies to RAP (with titers ranging from 1:50–1:16,000) as a result of the injections, whereas control animals did not. However, some of the animals contained pre-immune antibodies to RAP (titers ranging from 1:40–1:2000) and developed smaller lesions upon challenge with *S. aureus.* The titer of antibodies to RAP (in a total of 81 vaccinated or control animals) inversely correlated with lesion size (FIG. 2B). For purposes of this calculation, animals that died (of extensive cellulitis) were assumed to have a lesion size of 981 mm$^2$.

Mice vaccinated with RAP which purified from a *S. aureus* agr-null strain as described above had the same degree of protection as animals vaccinated with RAP which was purified from a wild-type strain. This rules out contribution of products from other genes known to regulate RNAIII, such as the octapeptide encoded by agrD (Guangyong et al. *Proc. Natl. Acad. Sci. U.S.A.* 92, 12055 (1995)).

TABLE 1

Vaccination with RAP as an antigen

| Treatment group | (total n) | no lesion n | (%) | lesion n | mean size (mm$^2$) | death n | (%) |
|---|---|---|---|---|---|---|---|
| RAP | (24) | 17 | (71) | 7 | (96) | 1 | (4) |
| RAP* | (9) | 7 | (78) | 2 | (84) | 0 | (0) |
| CFA | (10) | 3 | (30) | 10 | (177) | 2 | (20) |
| Untreated | (12) | 0 | (0) | 12 | (370) | 3 | (25) |

C. Purification and amino acid sequence of RIP

The non pathogenic *S. aureus* (ATCC 55619) produces the peptide RIP which inhibits RNAIII transcription (FIG. 3) and competes with RAP for the activation of virulence (Balaban et al., supra). HPLC-purified RIP (ibid) was submitted to Edman degradation sequencing. The amino acid sequence was determined to be YSPXTNF (SEQ ID NO:2), where X is a modified amino acid, C, I, or W, which has sequence homology to the NH$_2$-terminal sequence of RAP. Without being limited to any one theory, this suggests that gene encoding RIP may be a derivative of the gene encoding RAP.

Figure 3:
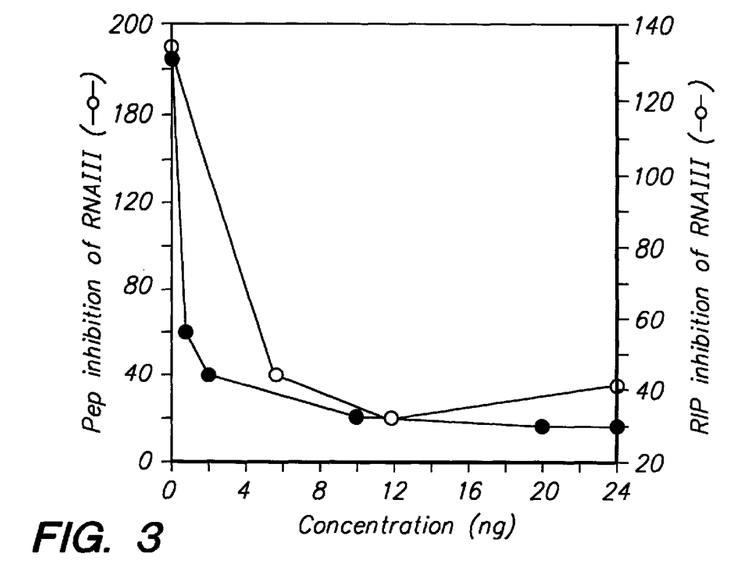
FIG. 3 is a graph depicting the inhibition of RNAIII by purified and synthetic RIP.

A synthetic peptide having the sequence YSPWTNF (SEQ ID NO:7) (denoted Pep herein) was synthesized and tested for its ability to inhibit RNAIII in vitro. The synthetic peptide inhibited induction of RNAIII comparably to RIP (FIG. 3).

D. Suppression of Infection by Purified RAP and RIP

Purified (Balaban et al, *Proc. Nal. Acad. Sci. U.S.A.* 92: 1619(1995)) and synthetic RIP were tested for their ability to suppress infection in the murine cutaneous *S. aureus* infection model. Smith Diffuse *S. aureus* ($8.5 \times 10^7$–$1.4 \times 10^9$) were incubated in the presence of RIP which was purified from 5 ml postexponential culture broth of ATCC 55619 in saline, or with saline only as a control, with 0.5 mg synthetic RIP (Pep) in a final DMSO (in saline) solution of 3%, or only with 3% DMSO in saline as a control, for 30 min at 37° C. The bacteria+RIP, bacteria+Pep, bacteria+saline or bacteria+DMSO mixture was injected subcutaneously together with cytodex beads (1 mg) into 8 week old male hairless immunocompetent mice to induce a local infection. The size of the lesion was measured daily. For these experiments mice were pre-screened to eliminate individuals with anti-RAP antibodies. A fixed amount of RIP (about 10 mg) attenuated infections caused by increasing inocula of the Smith Diffuse (SD) strain of *S. aureus.* Of the animals that were injected with $8.5 \times 10^7$ bacteria together with RIP, three of four developed no infection at all, as compared to only one of four control animals that were injected with the bacteria and saline (Table 2). When an increased inoculum of bacteria was used ($1.4 \times 10^8$ cells per injection), four of eight animals were protected, whereas the remaining four developed a lesion that was 55% smaller than that of control animals (Table 2). All (7/7) of the control animals challenged with SD and saline developed a lesion. When a higher number of bacteria was used ($1.4 \times 10^9$), the synthetic RIP (0.5 mg Pep) protected animals, where 90% (9/10) of the animals showed no sign of disease (Table 2).

TABLE 2

Vaccination or suppression of *S. aureus* SD infections

| Treatment group | (total n) | no lesion n | (%) | lesion n | mean size (mm$^2$) | death n | (%) |
|---|---|---|---|---|---|---|---|
| RIP Suppression of 8.5 × 10$^7$ SD | | | | | | | |
| SD + RIP | (4) | 3 | (75) | 1 | (33) | 0 | (0) |
| SD + Saline | (4) | 1 | (25) | 3 | (39) | 0 | (0) |
| RIP Suppression of 1.4 × 10$^8$ SD | | | | | | | |
| SD + RIP | (8) | 4 | (50) | 4 | (45) | 0 | (0) |
| SD + Saline | (6) | 0 | (0) | 6 | (100) | 0 | (0) |
| RIP and Pep Suppression of 1.4 × 10$^9$ SD | | | | | | | |
| SD + RIP | (10) | 3 | (30) | 0 | (0) | 4 | (40) |
| SD + Saline | (10) | 2 | (20) | 6 | (160) | 2 | (20) |
| SD + Pep | (10) | 9 | (90) | 1 | (56) | 0 | (0) |
| SD + DMSO | (9) | 2 | (20) | 4 | (128) | 3 | (22) |

E. Nucleotide Sequence of RIP

Degenerate oligonucleotides were designed from the amino acid sequence YSPWTNF (SEQ ID NO:7). The rip gene was amplified by PCR using Taq DNA polymerase. The PCR product was cloned into pCR2.1 (Invitrogen) and sequenced. The DNA sequence of the rip gene was determined to be TAT TCG CCG TGG ACC AAT TTT (SEQ ID NO:5).

F. Comparison of Synthetic and Natural RIP peptides

Figure 4A:
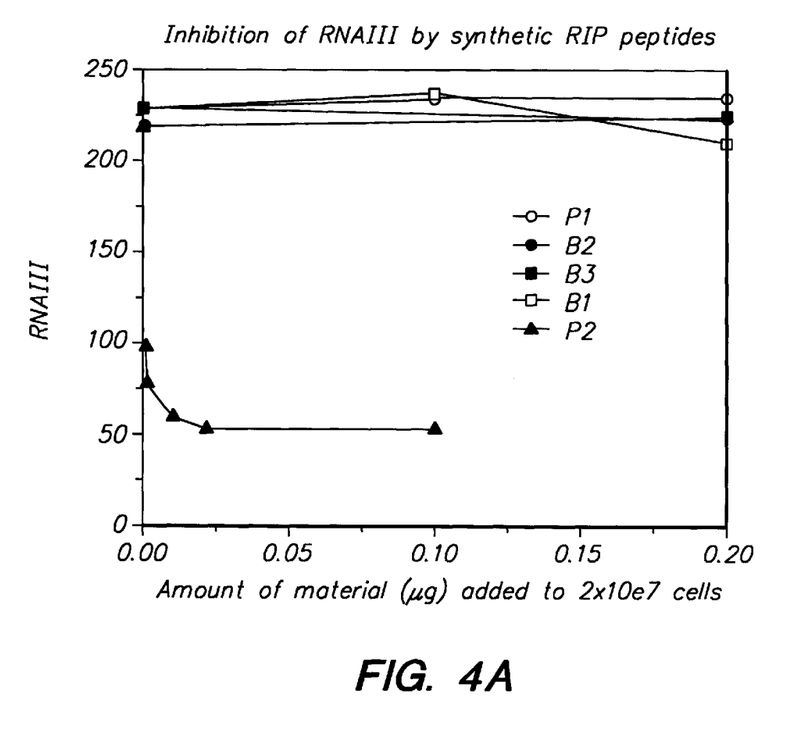
FIGS. 4A and 4B are graphs depicting the inhibition of RNAIII by synthetic RIP peptides.
Figure 4B:
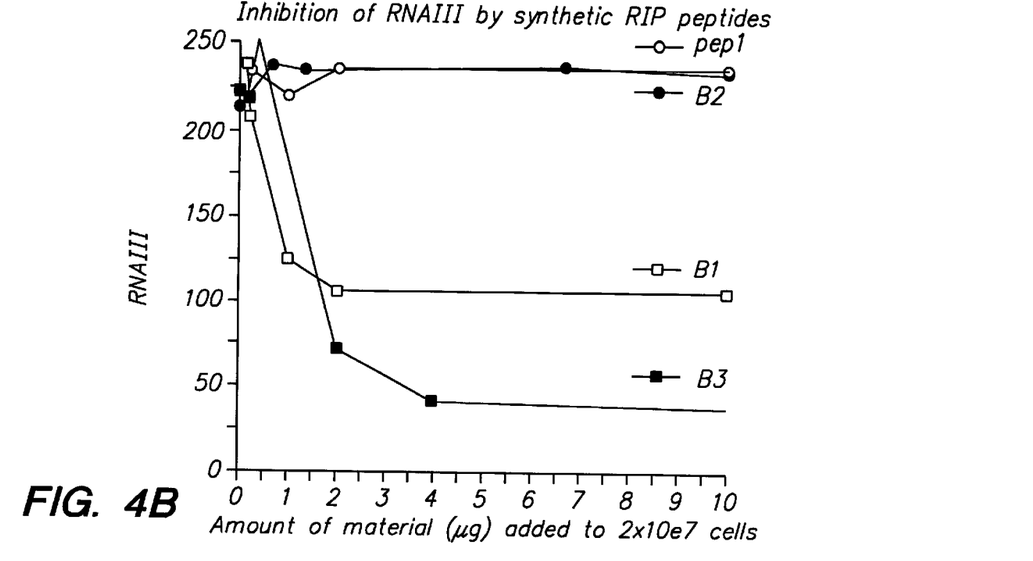
Figure 4C:
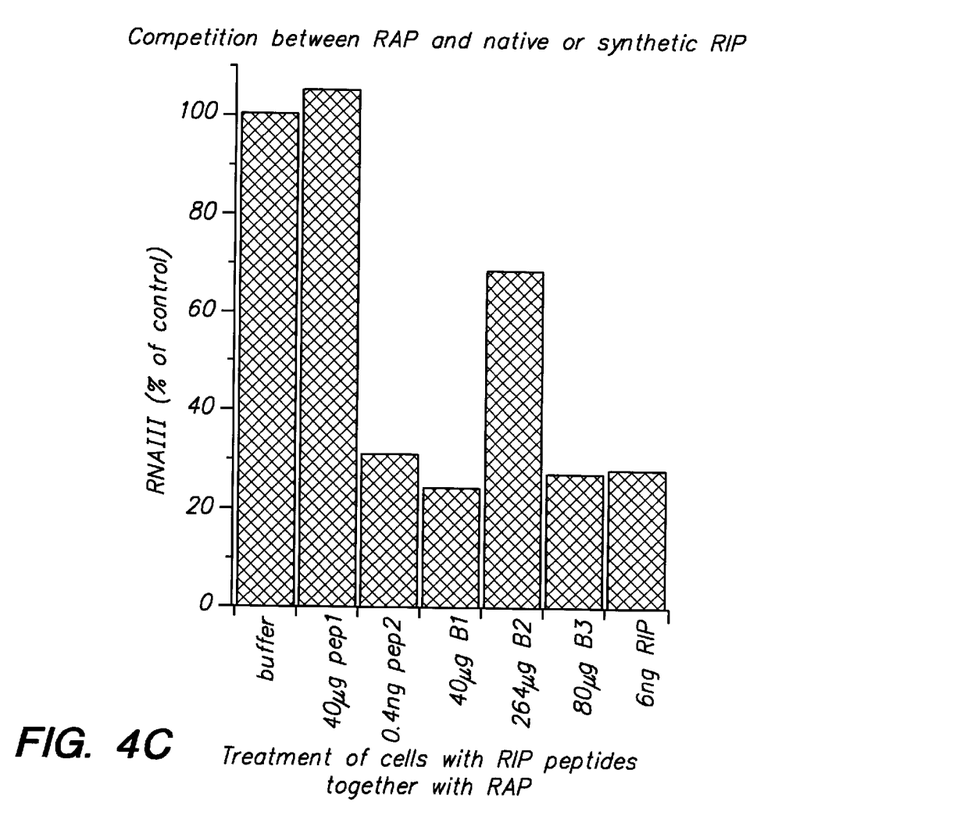
FIG. 4C is a graph depicting competition between RAP and purified or synthetic RIP.

Synthetic peptides corresponding to RIP were synthesized and tested for their ability to inhibit RNAIII in vitro (FIGS. 4A,B) or to compete with RAP on the activation of RNAIII (FIG. 4C). In those Figures RAP has the sequence IKKYK-PITN (SEQ ID NO:6); Pep 1 is PCTNF (SEQ ID NO:8); Pep2 is YSPWTNF (SEQ ID NO:7); B1 is YKPITNF (SEQ ID NO:9); B2 is YSPITIF (SEQ ID NO:10); and B3 is YKPWTNF (SEQ ID NO:11).

In these experiments RIP peptides or control buffer were added to $2\times10^7$ ATCC 55620 cells containing the agr P3-blaZ fusion plasmid. Cells were grown in a microtiter plate from early exponential phase of growth (before rnaiii is normally activated) for 2 hr (when rnaiii is normally activated) at 37° C. with shaking. The reaction was stopped by the addition of 10 $\mu$l CY containing azide. β-lactamase activity was measured by the addition of 50 $\mu$l nitrocefin (132 $\mu$g/ml in 0.1 M sodium phosphate buffer, pH 5.8) and read at 490–650 nm. To determine the competition between RAP and purified or synthetic RIP, RAP was added to cells in the presence or absence of RIP and RNAIII was measured 2 hr later. In summary, Pep2 inhibited RNAIII 100% at less than 1 ng; B1 inhibited RNAIII 50% at 2 $\mu$g; B2 inhibited RNAIII 50% at 66.6 $\mu$g; and B3 inhibited RNAIII 100% at 4 $\mu$g.

G. Discussion

Regulatory mechanisms involving autoinducers have been described for other bacterial systems (Rappuoli, et al. in: *Signal Transduction and Bacterial Virulence,* R. Rappuoli, V. Scarlato, B. Arico eds. (Springer Verlag, Heidelberg 1995). pp. 1–4.), including competence and sporulation in *Bacillus subtilis* and in *Streptococcus pneumoniae* (Magnuson et al. *Cell* 77, 207 (1994)), conjugation in *Enterococcus faecalis* (Swift et al, Trends in Microbiol. 2, 193 (1994)) and elastase production in Pseudomonas aeruginosa Pearson et al. *Proc. Natl. Acad. Sci. U.S.A.* 92, 1490 (1995)). Furthermore, compounds have been identified which inhibit the phosphorylation of the bacterial two component signal transduction system in *P. aeruginosa* Roychoudhury, et al, *Proc. Natl. Acad. Sci. U.S.A.* 90, 965 (1993)). Targeting the autoinducers of virulence or the signal transduction they activate may therefore be useful in preventing pathogenesis of other bacteria known to be regulated by global regulons.

Current bacterial vaccines target *S. aureus* or exotoxins it produces ((Lee, *Trends in Microbiol.* 4, 162 (1996)), R Naso and A Fattom, in: *Novel Strategies in Design and Production of Vaccines,* S. Cohen and A. Shafferman, eds. (Plenum Press, New York, 1996) pp. 133–140), but these approaches met with limited success. With an inexorable increase in antibiotic resistance among bacteria in general (Arthur et al., *Antimicrob. Agents and Chemother.* 37, 1563 (1993)) and among staphylococci in particular (Noble et al. *FEMS Microbiol. Lett.* 93, 195 (1992)), there is a need to develop new methods to control bacterial infections. Our approach is to interfere directly with bacterial virulence by interfering with the signal transduction that leads to the production of toxins. By reducing the pathogenic potential of the bacteria, this approach would be synergistic with current antimicrobial therapies and natural host immune mechanisms. Because directed suppression of virulence would not kill the bacteria but rather interfere with its pathogenicity, there would likely be a decrease in selective pressures for the emergence of new resistant *S. aureus* strains.

II. Analysis of cows for anti-RAP antibodies

Serum was collected from lactating dairy cows with one or more positive milk cultures for *S. aureus* (positive) and from lactating cows that have no record of having clinical case of *S. aureus* mastitis through one lactation (negative) (Table 3A) and from calves which are 1 month and 4 months old (Table 3B). Sera were tested for anti-RAP antibodies by western blotting against post exponential supernatants of wild type *S. aureus*-containing RAP. As shown in Table 3A, only 10% (2/20) of *S. aureus*-positive cows contain anti-RAP antibodies, while 63% (7/11) of *S. aureus*-negative cows contain anti-RAP antibodies. As shown in Table 3B, 38–46% of the calves contained anti-RAP antibodies. *S. aureus*-negative cows as well as calves will be followed in the future for correlation between titer of anti-RAP antibodies and natural infection rates. As also shown in Table 3A, 60% (12/20) of the positive cows as compared to 18% (2/11) of the negative cows also contained antibodies to various unidentified proteins in *S. aureus* supernatant (presumed to be antibodies to other *S. aureus* proteins).

Thus, these data indicate that a majority of dairy cows that are negative for *S. aureus* mastitis naturally contain anti-RAP antibodies. These results support the use of RAP as a useful vaccine target site for the prevention of staphylococcal infections.

TABLE 2A

| Anti-RAP Antibodies in Cows | | | | |
|---|---|---|---|---|
| Cow | n | RAP | other *S. aureus* proteins | no anti-*S. aureus* |
| negative | 11 | 7 (63%) | 2 (18%) | 1 (18%) |
| positive | 20 | 2 (10%) | 12 (60%) | 6 (30%) |
| Anti-RAP Antibodies in Calves | | | | |
| Calves | n | RAP | other *S. aureus* proteins | no anti-*S. aureus* |
| 1 month old | 20 | 5 (38%) | 2 (10%) | 13 (65%) |
| 4 months old | 20 | 6 (46) | 1 (5) | 13 (65%) |

All publications and patent applications cited in this specification are herein incorporated by reference in their entirety as if each individual publication or patent application were specifically and individually indicated to be incorporated by reference.

As will be apparent to those skilled in the art to which the invention pertains, the present invention may be embodied in forms other than those specifically disclosed above, without departing from the spirit or essential characteristics of the invention. The particular embodiments of the invention described above, are, therefore to be considered as illustrative and not restrictive. The scope of the present invention is as set forth in the appended claims rather than being limited to the examples contained in the foregoing description.

We claim:

1. A method for treating a host having or at risk of a staphylococcal infection, the method comprising:
    administering to a host a composition comprising a polypeptide, the polypeptide comprising an amino acid sequence of the general formula Y(K or S)PXTNF, where X is C, W, or I.
2. The method of claim 1, wherein the host is a human.
3. The method of claim 1, wherein the host is an animal.
4. The method of claim 3, wherein the animal is an experimental animal.
5. The method of claim 1, wherein the composition is administered after onset of symptoms.
6. The method of claim 1, wherein the composition is administered prophylactically.

7. A method for treating a staphylococcal infection in an infected animal host, the method comprising administering an antagonist of an RNAIII Activating protein (RAP) receptor to the host.

8. The method of claim 7, wherein the host is a human subject.

9. The method of claim 7, wherein the animal host is a bovine animal.

10. The method of claim 7, wherein the RAP receptor antagonist is a polypeptide.

11. The method of claim 7, wherein the antagonist is an anti-RAP antibody.

12. A method for inhibiting staphylococcal infection in an animal host, the method comprising administering an antagonist of a RNAIII Activating protein (RAP) receptor to the host.

13. The method of claim 12, wherein the host is a human.

14. The method of claim 12, wherein the animal host is a bovine animal.

15. The method of claim 12, wherein the RAP receptor antagonist is a polypeptide.

16. The method of claim 12, wherein the RAP receptor antagonist is an antibody that specifically binds a RAP receptor ligand.

17. The method of claim 12, wherein the antagonist is an anti-RAP antibody.

18. The method of claim 12, wherein said administering is prior to staphylococcal infection.

19. The method of claim 1, wherein the polypeptide comprises the amino acid sequence YKPXTNF, where X is C, W, or I.

20. The method of claim 1, wherein the polypeptide comprises the amino acid sequence YKPCTNF.

21. The method of claim 1, wherein the polypeptide comprises the amino acid sequence YKPWTNF.

22. The method of claim 1, wherein the polypeptide comprises the amino acid sequence YKPITNF.

23. The method of claim 1, wherein the polypeptide comprises the amino acid sequence YSPXTNF, where X is C, W, or I.

24. The method of claim 1, wherein the polypeptide comprises the amino acid sequence YSPCTNF.

25. The method of claim 1, wherein the polypeptide comprises the amino acid sequence YSPWTNF.

26. The method of claim 1, wherein the polypeptide comprises the amino acid sequence YSPITNF.

* * * * *